United States Patent
Jackson et al.

(10) Patent No.: US 11,602,757 B2
(45) Date of Patent: Mar. 14, 2023

(54) METHOD OF EXTRACTING MATERIAL FROM A FLUID AND EXTRACTOR

(71) Applicant: Randox Laboratories Ltd., Crumlin (GB)

(72) Inventors: Stuart Jackson, Crumlin (GB); Stephen Peter Fitzgerald, Crumlin (GB); Ivan McConnell, Crumlin (GB); John Lamont, Crumlin (GB)

(73) Assignee: RANDOX LABORATORIES LTD., Crumlin (GB)

( * ) Notice: Subject to any disclaimer, the term of this patent is extended or adjusted under 35 U.S.C. 154(b) by 994 days.

(21) Appl. No.: 16/341,436

(22) PCT Filed: Oct. 13, 2017

(86) PCT No.: PCT/GB2017/053106
§ 371 (c)(1),
(2) Date: Apr. 11, 2019

(87) PCT Pub. No.: WO2018/069724
PCT Pub. Date: Apr. 19, 2018

(65) Prior Publication Data
US 2020/0038877 A1 Feb. 6, 2020

(30) Foreign Application Priority Data
Oct. 13, 2016 (GB) ...................... 1617388

(51) Int. Cl.
*B01F 33/452* (2022.01)
*C12N 15/10* (2006.01)
(Continued)

(52) U.S. Cl.
CPC .............. *B03C 1/01* (2013.01); *B01F 33/452* (2022.01); *B03C 1/288* (2013.01); *C12N 15/1013* (2013.01); *B01F 2101/23* (2022.01)

(58) Field of Classification Search
CPC .. B03C 1/01; B03C 1/288; B03C 1/23; B03C 1/24; B03C 1/32; B01F 33/452;
(Continued)

(56) References Cited

U.S. PATENT DOCUMENTS 6,764,859 B1 * 7/2004 Kreuwel ............... B03C 1/0332
536/25.4
2007/0056912 A1 * 3/2007 Oder ...................... C10G 2/342
210/695

(Continued)

FOREIGN PATENT DOCUMENTS

CN 106 754 345 A 5/2017
CN 106754345 A * 5/2017
(Continued)

OTHER PUBLICATIONS

Fourgeaud, Damien, International Search Report and Written Opinion, European Patent Office, PCT/GB2017/053106, dated Jan. 12, 2018.
(Continued)

*Primary Examiner* — Gene O Crawford
*Assistant Examiner* — Muhammad Awais
(74) *Attorney, Agent, or Firm* — Gavrilovich, Dodd & Lindsey LLP

(57) ABSTRACT

There is provided a method of extracting material from a fluid method of extracting material from a fluid, the fluid being held within a fluid chamber. The method comprises drawing, with a magnetic field generating system, at least one magnetically susceptible member through the fluid around a closed path between at least three points in the chamber, said at least one member being adapted to bind to material in fluid in the chamber. The at least three points are arranged relative to each other in a shape having at least two dimensions, the magnetic field generating system being
(Continued)

configured to move the at least on magnetically susceptible member directly between the at least three points, material in the fluid binding to the at least one magnetically susceptible member when it comes into contact with the at least one member as it moves through the fluid.

23 Claims, 8 Drawing Sheets

(51) Int. Cl.
*B03C 1/01* (2006.01)
*B03C 1/28* (2006.01)
*B01F 101/23* (2022.01)

(58) Field of Classification Search
CPC .... B01F 2101/23; B01F 33/30; B01F 33/451; C12N 15/1013; B01D 15/3885
USPC ......................................................... 210/222
See application file for complete search history.

(56) References Cited

U.S. PATENT DOCUMENTS

| | | | |
|---|---|---|---|
| 2007/0215554 A1* | 9/2007 | Kreuwel | B03C 1/0332 210/695 |
| 2011/0198294 A1 | 8/2011 | Sharpe | |
| 2012/0132593 A1* | 5/2012 | Murthy | C12M 47/02 209/636 |
| 2012/0261348 A1* | 10/2012 | Roh | B03C 1/288 210/695 |
| 2013/0225421 A1* | 8/2013 | Li | C12Q 1/686 506/26 |
| 2013/0344477 A1* | 12/2013 | Parton | C12Q 1/24 435/5 |
| 2015/0247185 A1* | 9/2015 | Murayama | B03C 1/288 536/25.4 |
| 2016/0180998 A1* | 6/2016 | Kanai | G01N 35/0098 210/222 |
| 2016/0194684 A1 | 7/2016 | Lemonnier | |

FOREIGN PATENT DOCUMENTS

| | | | | |
|---|---|---|---|---|
| EP | 1 589 105 A1 | 10/2005 | | |
| EP | 1 621 890 A1 | 2/2006 | | |
| EP | 1 658 890 A2 | 5/2006 | | |
| JP | 2012110279 A | * 6/2012 | | |
| WO | 01/05510 A1 | 1/2001 | | |
| WO | WO-2012118221 A1 | * 9/2012 | ........... B03C 1/0332 | |
| WO | WO-2016051795 A1 | * 4/2016 | .............. B01L 3/502 | |

OTHER PUBLICATIONS

Lloyd, Beverley, Search Report, Application No. GB1617388.2, U.K. Intellectual Property Office, dated Apr. 13, 2017.

* cited by examiner

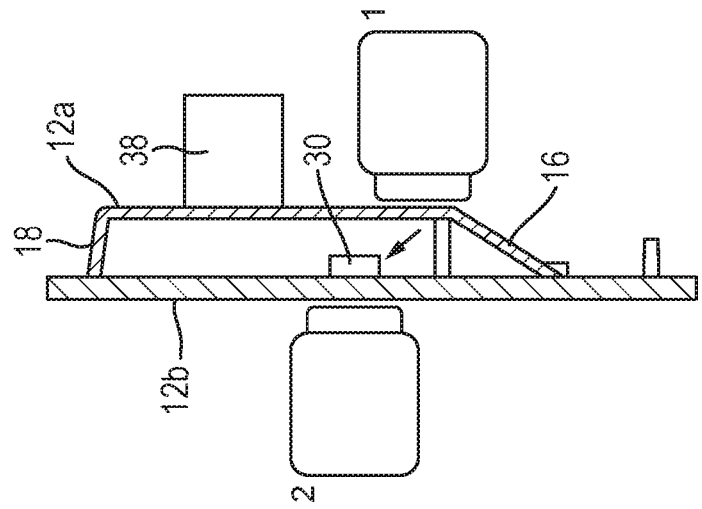
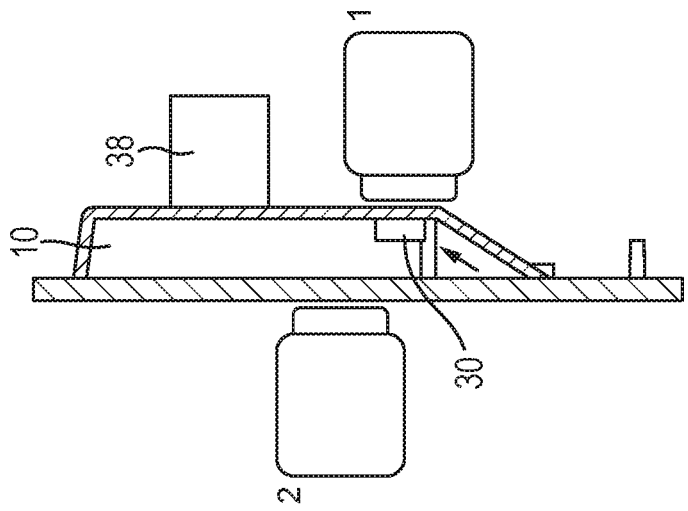
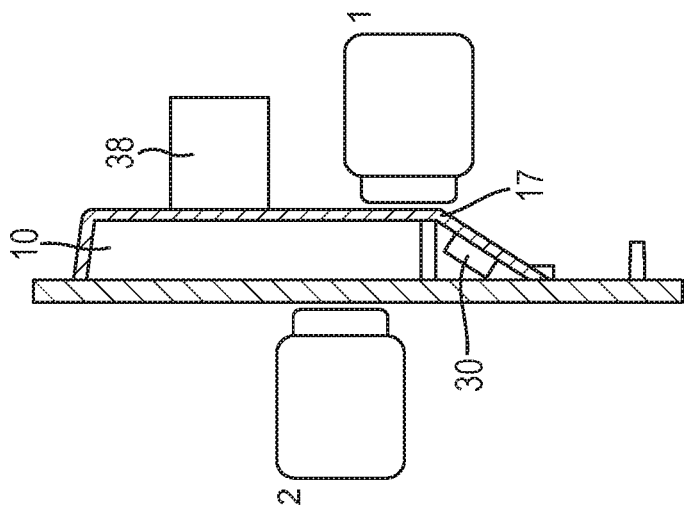

METHOD OF EXTRACTING MATERIAL FROM A FLUID AND EXTRACTOR

CROSS REFERENCE TO RELATED APPLICATION

This application is a U.S. National Stage Application filed under 35 U.S.C. § 371 and claims priority to International Application No. PCT/GB2017/053106, filed Oct. 13, 2017, which application claims priority to Great Britain Application No. 1617388.2, filed Oct. 13, 2016, the disclosures of which are incorporated herein by reference in their entireties.

FIELD OF THE INVENTION

The present invention relates to extracting material from a fluid. In particular it relates to extracting material, such as DNA or RNA, from a sample using a magnetically susceptible member.

BACKGROUND

In biological, medical and forensic analysis, as well as in other situations, extraction of DNA or RNA from a solution, also known as DNA purification and RNA purification respectively, is a commonly conducted process. Such DNA and RNA extraction typically involves highly skilled operatives and expensive, complicated machinery with many disposable consumables, and acceptable yields of DNA or RNA are often only obtainable after a number of steps.

There are a number of methods available to remove DNA and RNA from a solution. Most of these methods involve filtering through a silicon based material, using a spin column or imparting pressure on the solution. A further method of removing DNA and RNA from a solution is to mix the solution with magnetic beads that have a treated surface that can bind specifically to DNA and/or RNA.

The known methods, such as that disclosed in US 2015/0368636 A1, of removing DNA and RNA by the use of magnetic beads require a mechanical method to mix the beads in the solution so that the binding occurs. Once the mixing has been conducted, a permanent magnet then facilitates removal of the beads, now with the DNA and/or RNA bound to them, from the solution. This causes difficulty because such a process involves a number of steps using equipment with various moving parts. Additionally, if the process is performed manually, there is a chance that there will be contamination of the sample and/or the environment in which the process is conducted due to the need to remove the beads from the container in which the solution is held. An automated machine that carries out the process also has disadvantages in that the machine requires the user to place a number of consumables, such as solution containers into the machine before it runs the process (also known as an assay). Furthermore, the automated process takes a long time to complete, typically lasting at least 30 minutes.

Known automated processes involve bulky machinery with many moving parts that process many consumables. The machinery generally uses aggressive agitation to mix the magnetic beads, such as instigating turbulence by means of a physical plunger or by agitation. Such machinery is only suitable for use in a laboratory, not at the point of care, such as at a bedside, in a doctor's surgery or a clinic.

Accordingly, there is a need for more compact and simple machinery and for the process to be less wasteful to allow such automated extraction of DNA and RNA to be conducted at the point of care. To be used at the point of care, there is also a need for the process and machinery to be reliable, efficient and robust to withstand the repeated user and to minimise the amount of time taken over the extraction.

SUMMARY OF INVENTION

According to a first aspect of the invention, there is provided a method of extracting material from a fluid, the fluid being held within a fluid chamber, the method comprising: drawing, with a magnetic field generating system, at least one magnetically susceptible member through the fluid around a closed path between at least three points in the chamber, said at least one member being adapted to bind to material in fluid in the chamber, wherein the at least three points are arranged relative to each other in a shape having at least two dimensions, the magnetic field generating system being configured to move the at least one magnetically susceptible member directly between the at least three points, material in the fluid binding to the at least one magnetically susceptible member when it comes into contact with the at least one member as it moves through the fluid.

Moving the at least one magnetically susceptible member around the fluid chamber in this manner causes the at least one magnetically susceptible member to move through a substantial amount of fluid while minimising any superfluous movement thereby minimising energy usage required to move the at least one magnetically susceptible member. This allows significant amounts of material, such as DNA and/or RNA to be removed from the fluid, while providing an energy efficient system.

By the term "directly", it is intended to mean that the movement is generally in a straight line. In other words, we intend to mean that movement directly between the at least three points involves movement only between those at least three points with travel between each of the at least three points being along the shortest path between adjacent points.

By the term "magnetically susceptible", it is intended to mean that the member(s) have a positive magnetic susceptibility. In other words, we intend to mean that the at least one magnetically susceptible member is attracted into a magnetic field external to the at least one member instead of being repelled out of such a magnetic field. Examples of material types that are intended to be included in within this meaning are ferromagnetic materials, ferrimagnetic materials, antiferromagnetic materials and paramagnetic materials.

The magnetic field generating system may be configured to draw the at least one magnetically susceptible member around the closed path in any suitable manner. Typically, the magnetic field generating system is configured to draw the at least one magnetically susceptible member to two of the at least three points using a magnetic field and to allow the at least one magnetically susceptible member to travel to the third point of the at least three points without using a magnetic field. This further reduces the energy consumption of the system when in use. As such, this improves the energy efficiency of the system.

The at least one magnetically susceptible member may be drawn around the closed path by only by the magnetic field generating system. However typically, the at least one magnetically susceptible member is allowed to travel to the third point of the at least three points under the influence of gravity. This removes the need for the magnetic field generating system, or any other mechanism, to be used to generate a force to cause the at least one magnetically susceptible member to move to the third point of the at least three points. This simplifies the magnetic field generating system and reduces the component count of the magnetic field generating system and therefore the system as a whole.

The magnetic field generating system may use permanent magnets. Typically however, the magnetic field generating system comprises at least one electromagnet. This means that no moving parts are needed outside the fluid chamber. This reduces wear on the components and therefore improves reliability. Additionally, this reduces the number of moving parts outside of the fluid chamber allowing the apparatus in which the chamber is housed to be smaller. This is advantageous as it allows the apparatus to be used at the point of care, instead of only on a lab bench.

Movement of the at least one magnetically susceptible member may be in any direction relative to a magnetic field produced by the magnetic field generating system, such as perpendicular to the field. Typically, movement of the at least one magnetically susceptible member caused by operation of the magnetic field generating system is towards a magnetic pole of the at least one electromagnet.

The movement of the at least one magnetically susceptible member towards a magnetic pole allows a weaker electromagnet to be used than if the movement was only through the magnetic field. This is because the at least one magnetically susceptible member is moved at least in part due to attraction to the nearest pole of the at least one electromagnet instead of just moving due to a force produced by the magnetic field. This means that less power is used by the electromagnet thereby making the apparatus more energy efficient.

Heating the fluid in the chamber improves the binding of the material in the fluid to the at least one magnetically susceptible member. The fluid may be heated by any type of heater. Typically, the method further comprises the step of heating the fluid in the chamber with heat produced by the at least one electromagnet. This means that no additional heater is needed and uses the by-product of the magnetic field generation thereby improving the overall efficiency of the apparatus causing it to use less power than if a further heater were to be used.

The fluid chamber may be any suitable shape and the drawing of the at least one magnetically susceptible member between the at least three points of the closed path may be conducted in any suitable manner. In a first configuration typically, the fluid chamber comprises a side wall connected to a base and orientated such that contents of the chamber are pulled towards the base under the influence of gravity, the base being inclined to the vertical, and wherein the step of drawing the at least one magnetically susceptible member through the fluid around the closed path between the at least three points in the chamber comprising: drawing, with the magnetic field generating system, the at least one magnetically susceptible member along the base to the side wall connected at an upper end of the base; moving, with the magnetic field generating system, the at least one magnetically susceptible member through the fluid away from the side wall connected at the upper end of the base; and allowing the at least one magnetically susceptible member to return to the base.

Due to the incline of the base, the resultant force on the at least one magnetically susceptible member along the base imposed by gravity and the pressure applied by the fluid on the at least one magnetically susceptible member is reduced relative to the at least one magnetically susceptible member being on a horizontal surface. This reduces the amount of force required to draw the at least one magnetically susceptible member up the inclined base to the side wall at the upper end of the base. In turn, this means that the magnetic field(s) produced by the magnetic field generating system are able to be weaker to achieve the same result. This allows weaker magnets to be used to remove material from the fluid.

Moving the at least one magnetically susceptible member through the fluid away from the side wall connected at the upper end of the base may include moving the at least one magnetically susceptible member only part of the way across the chamber. Typically however, moving the at least one magnetically susceptible member through the fluid away from the side wall connected at the upper end of the base comprises moving the at least one magnetically susceptible member across the chamber to the side wall above the connection to the base at the lower end of the base.

Moving the at least on magnetically susceptible member from one side wall to an opposing side wall lengthens the path followed by the at least one magnetically susceptible member when being moved around the fluid chamber. This causes the at least one magnetically susceptible member to move through more of the fluid allowing the at least one magnetically susceptible member to come in contact with more material within the fluid. This increases the amount of material that will become bound to the at least one magnetically susceptible member improving the efficiency with which the material is removed from the fluid.

The at least one magnetically susceptible member may only be moved horizontally when moved away from the side wall connected at the upper end of the base. Typically though, the magnetically susceptible member is moved vertically away from the base when moved away from the side wall connected at the upper end of the base. This also lengthens the path followed by the at least one magnetically susceptible member. Accordingly, this produces the same advantage as when the at least one magnetically susceptible member is moved across the chamber from one side wall to the other. When combined, the effect is multiplied.

The steps of drawing the magnetically susceptible member along the base, moving said member through the fluid away from the side wall and allowing said member to return to the base may only be conducted once. Preferably however, the steps of drawing the magnetically susceptible member along the base, moving said member through the fluid away from the side wall and allowing said member to return to the base are repeated in a cycle.

Repeating the drawing, moving and returning steps in a cycle causes the fluid in the chamber to move, which mixes the fluid. Additionally, movement of the at least one magnetically susceptible member causes turbulence in the fluid causing further mixing. This mixing of the fluid increases the amount of material that is removed from the fluid by the at least one magnetically susceptible member. This is because the mixing process acts to homogenise the fluid in which the material is present.

Typically, the method further comprises the step of mixing the fluid with a mixing system. The mixing system may preferably be a vibration motor. This is advantageous as it allows more effective mixing of the fluid in the chamber causing a greater amount of binding of the material to the at least one magnetically susceptible member to occur. When there are a plurality of magnetically susceptible members, the vibration motor also reduces clumping of these members.

The at least one magnetically susceptible member may be returned to the base by the application of a magnetic force, but typically, the at least one magnetically susceptible member is allowed to return to the base under the influence of gravity. As mentioned above, this removes the need for the magnetic field generating system, or any other mechanism to be used to generate a force to cause the at least one magnetically susceptible member to return to the base of the fluid chamber. This simplifies the magnetic field generating system.

When the magnetic field generating system comprises at least one electromagnet, movement of the at least one magnetically susceptible member may be produced by only one magnet, but typically, the at least one magnetically susceptible member is drawn along the base by a first electromagnet and moved through the fluid away from the side wall by a second electromagnet. This allows a simple control of electromagnets instead of complex control that would be required otherwise. This means the apparatus is simpler to manufacture and reduces the complexity of the control system for the magnetic field generating system.

In a second configuration typically, the fluid chamber comprises an extraction portion and an elution portion, the elution portion having a smaller volume than the extraction portion and having a top opening into a base of the extraction portion, the method further comprising: drawing, with the magnetic field generating system, the at least one magnetically susceptible member between the extraction and elution portions of the chamber; and removing material bound to the at least one magnetically susceptible member from the at least one magnetically susceptible member when in the elution portion by replacing the fluid in the chamber with an eluent held in only the elution portion.

Prior to developing the second configuration, when using a fluid chamber, such as a fluid chamber as set out in the first configuration, we found that this at times resulted in the concentration of the material in the eluent being too low for further processing, such as amplification using PCR. In order to try to achieve improved concentration of the material in the fluid into which the material is passed following extraction from a sample fluid, the at least one magnetically susceptible member was instead passed into a smaller chamber from the fluid chamber. This process was applied so as to use a smaller volume of eluent in order to increase the concentration of material in the eluent. However, a further issue occurred in that the at least one magnetically susceptible member was found to either block a fluid channel or become lost in a channel between the two chambers (movement being achieved through magnetic attraction).

We found that being able to draw the at least one magnetically susceptible member between the extraction portion and the elution portion allows material to be extracted from the fluid in the extraction portion while allowing material to be removed from the at least one magnetically susceptible member in the elution portion is advantageous. This is because, due to the larger volume of the extraction portion, the at least one magnetically susceptible member is able to pass through larger quantities of fluid. This increases the amount of material that is able to be extracted from the fluid over seeking to extract the material in a smaller volume portion. Additionally, the smaller volume of the elution portion allows the concentration of the material in the eluent to be improved over concentrations able to be achieved in a larger volume. As such, the overall advantage of this is that larger quantities of material are able to be extracted from a sample while allowing improvements in concentration of the material in the fluid into which the material is passed.

The at least three points may be located in any arrangement. However, typically the at least three points form a configuration corresponding to the vertices of a triangle. In other words, the at least three points may form the vertices of a triangle. This allows the at least one magnetically susceptible member to be moved along a triangular path. This causes the fluid to circulate, which brings the at least one magnetically susceptible member into contact with more material while minimising the number of points to which the at least one magnetically susceptible member travels. This therefore minimises energy usage.

Preferably, two of the vertices have the same separation along a longitudinal axis of the chamber from the base of the extraction portion of the chamber. This allows the at least one magnetically susceptible member to be moved across the chamber along the shortest possible path across the chamber minimising the energy required to move the at least one magnetically susceptible member across the chamber.

The third vertex may be located at any suitable point relative to the other two vertices, such as at a position with a smaller separation from the base of the extraction portion, though typically, the third vertex has a greater separation along the longitudinal axis of the chamber than the other two vertices from the base of the extraction portion of the chamber. This allows gravity to contribute to movement of the at least one magnetically susceptible member between at least two of the vertices thereby reducing the amount of energy used by the magnetic field generating system on that part of the movement. Further, this causes the fluid to circulate within the chamber drawing fluid and material from above and below the movement path to bring the at least one magnetically susceptible member into contact with more material.

As mentioned above, the at least one magnetically susceptible member may be drawn around the closed path by only by the magnetic field generating system, but typically, in this configuration, the at least one magnetically susceptible member is allowed to move between the third vertex and one of the two other vertices under the influence of gravity. As mentioned above, this removes the need for the magnetic field generating system, or any other mechanism to be used to generate a force to cause the at least one magnetically susceptible member to move to the third vertex. This simplifies the magnetic field generating system and reduces the component count of the magnetic field generating system and therefore the system as a whole.

Preferably, the step of drawing the at least one magnetically susceptible member through the fluid around the closed path between the at least three points in the chamber may comprise: moving, with the magnetic field generating system, the at least one magnetically susceptible member through the fluid from a first side wall of the extraction portion of the chamber away from the first side wall. This allows the whole of the surface of the at least one magnetically susceptible member to be exposed to the fluid, which increases the amount of material with which the at least one magnetically susceptible member is able to bind.

The first side wall may be any side wall of the extraction portion and may be any suitable shape or form. Typically, the first side wall is a single continuous wall forming a side wall of the extraction portion and the elution portion. This allows the wall to provide a guide for the at least one magnetically susceptible member when being drawn between the extraction portion and the elution portion.

Preferably, moving the at least one magnetically susceptible member through the fluid away from the side may comprise moving the at least one magnetically susceptible member across the chamber to a second side wall, the second side wall being an opposing side wall of the extraction portion to the first side wall. As mentioned above, moving the at least on magnetically susceptible member from one side wall to an opposing side wall lengthens the path followed by the at least one magnetically susceptible member when being moved around the fluid chamber. This causes the at least one magnetically susceptible member to move through more of the fluid allowing the at least one magnetically susceptible member to come in contact with more material within the fluid. This increases the amount of material that will become bound to the at least one magnetically susceptible member improving the efficiency with which the material is removed from the fluid.

When the magnetic field generating system comprises at least one electromagnet, preferably drawing the at least one magnetically susceptible member between the extraction and elution portion of the chamber may comprise moving at least one electromagnet of the at least one electromagnets between the extraction and elution portion while retaining the at least one magnetically susceptible member in a magnetic field generated by said at least one electromagnet. This allows controlled movement of the at least one magnetically susceptible members between the elution and extraction portions, which keeps the magnetic field generating system simple by avoiding the need for separate magnetic field generating components in the extraction and elution portions.

As with the first configuration, in the second configuration, movement of the at least one magnetically susceptible member may be produced by only one magnet, but typically, the at least one magnetically susceptible member is drawn across the extraction portion from the first side wall to the second side wall by a second electromagnet and moved through the fluid form the second side wall to the first side wall by the other (or "first") electromagnet. This allows a simple control of electromagnets instead of complex control that would be required otherwise. This means the apparatus is simpler to manufacture and reduces the complexity of the control system for the magnetic field generating system. In this arrangement it is typically the first electromagnet that is able to move the at least one magnetically susceptible member between the extraction and elution portions.

The base of the extraction portion may be any suitable shape. Typically, the base of the extraction portion is shaped to form a funnel, a narrow end of the funnel being connected to the elution portion and a wide end of the funnel being connected to side walls of the extraction portion. This allows the contents of the chamber, whether that is the at least one magnetically susceptible member and/or any fluid to be directed towards the elution portion under the influence of gravity providing a higher rate of flow into the elution portion than an arrangement in which there is no funnel.

Returning to the first aspect in general, as set out above, the at least one magnetically susceptible member may be ferromagnetic, ferrimagnetic or antiferromagnetic. Typically though, the at least one magnetically susceptible member is at least one paramagnetic member. This causes that the magnetic field induced in the at least one magnetically susceptible member when the member to dissipate when the member is not in a magnetic field. This means that when no magnetic field is being applied to the chamber, there is no residual magnetic field or effect remaining. This is advantageous because there is not residual magnetism that is able to disrupt anything outside of the apparatus when it is not in use.

The fluid chamber may have any cross-section across a horizontal plane, such as circular or elliptical. Typically however, the side wall comprises a pair of opposing side walls, one side wall of which is connected to the upper end of the base and the other side wall of which is connected to the lower end of the base.

This allows the fluid chamber to have the largest possible volume for the space in which it is located and provides flat surfaces against which components can be located to minimise the amount of wasted or unused space.

The material that is extracted from the fluid in the chamber may be any material, such as any material that can be caught by a coated magnetic bead, or that has an inherent magnetic affinity such as bacteria (for example, *Acidithiobacillus ferrooxidans*) or "d-band" materials (i.e. materials which have an electronic band structure with a partially filled d-band). Typically, the material is DNA and/or RNA. Additionally, the fluid may be any fluid. Preferably however, the fluid is a liquid such as fungal liquor, water, milk, wine, honey, syrup or body fluids, including serum, urine, vaginal fluid, semen, pus, cerebral fluid, blood or sputum.

The at least one magnetically susceptible member may be adapted to bind to material in fluid in any way. Typically, the at least one magnetically susceptible member has a coating to which material in fluid in the chamber binds. This provides a simple way for material in fluid in the chamber to bind to the at least one magnetically susceptible member. Preferably, the coating is streptavidin.

According to a second aspect of the invention, there is provided a method of extracting material from a fluid, the fluid being held within a fluid chamber comprising a side wall connected to a base and orientated such that contents of the chamber are pulled towards the base under the influence of gravity, the base being inclined to the vertical, the method comprising the steps: drawing, with a magnetic field generating system, at least one magnetically susceptible member adapted to bind to material in fluid in the chamber along the base to the side wall connected at an upper end of the base; moving, with said magnetic field generating system, the at least one magnetically susceptible member through the fluid away from the side wall connected at the upper end of the base; and allowing the at least one magnetically susceptible member to return to the base.

As mentioned above, moving the at least one magnetically susceptible member around the fluid chamber in this manner causes the at least one magnetically susceptible member to move through a substantial amount of fluid. This allows significant amounts of material, such as DNA and/or RNA to be removed from the fluid.

Additionally, due to the incline of the base, the resultant force on the at least one magnetically susceptible member along the base imposed by gravity and the pressure applied by the fluid on the at least one magnetically susceptible member is reduced relative to the at least one magnetically susceptible member being on a horizontal surface. This reduces the amount of force required to draw the at least one magnetically susceptible member up the inclined base to the side wall at the upper end of the base. In turn, this means that the magnetic field(s) produced by the magnetic field generating system are able to be weaker to achieve the same result. This allows weaker magnets to be used to remove material from the fluid.

According to a third aspect of the invention, there is provided a method of extracting material from a fluid, the fluid being held within a fluid chamber comprising an extraction portion and an elution portion, the elution portion having a smaller volume than the extraction portion and having a top opening into a base of the extraction portion, the method comprising the steps: drawing, with a magnetic field generating system, at least one magnetically susceptible member adapted to bind to material in fluid in the chamber between the extraction and elution portions of the chamber; moving, with said magnetic field generating system, the at least one magnetically susceptible member through the fluid between side walls of the chamber; and removing material bound to the at least one magnetically susceptible member from the at least one magnetically susceptible member when in the elution portion by replacing the fluid in the chamber with an eluent held in only the elution portion.

As mentioned above, using the method of the third aspect we found that, due to the larger volume of the extraction portion, the at least one magnetically susceptible member is able to pass through larger quantities of fluid. This increases the amount of material that is able to be extracted from the fluid over seeking to extract the material in a smaller volume portion. Additionally, the smaller volume of the elution portion allows the concentration of the material in the eluent to be improved over concentrations able to be achieved in a larger volume. As such, the overall advantage of this is that larger quantities of material are able to be extracted from a sample while allowing improvements in concentration of the material in the fluid into which the material is passed.

The at least one magnetically susceptible member may be moveable by movement of at least part of the magnetic field generating system. Such movement may be movement of the at least one electromagnet. The movement may be movement along an axis aligned with a length of the chamber. The range of movement may include an ability to align the at least one electromagnet with the base of the chamber. This allows movement of the at least one magnetically susceptible member to be caused by movement of the at least part of the magnetic field generating system. Should the at least one magnetically susceptible member become located in a position where the magnetic field is unable to move the at least one magnetically susceptible member in a standard position, this allows the at least one magnetically susceptible member to be moved. When there are a plurality of magnetically susceptible members, should said members have become clumped at the bottom of the chamber, the ability to move at least a part of the magnetic field generating system allows a magnetic field to be used to move said members from the bottom of the chamber since this alters the magnetic field.

According to a fourth aspect of the invention, there is provided an extractor for extracting material from a fluid, comprising: a fluid chamber comprising a side wall connected to a base and orientated such that contents of the chamber are pulled towards the base under the influence of gravity, the base being inclined to the vertical, the chamber being adapted to contain at least one magnetically susceptible member, said at least one magnetically susceptible member being adapted to bind to material in fluid in the chamber; and a magnetic field generating system associated with the fluid chamber, which generating system is operable to cause the at least one magnetically susceptible member to move around a closed path including the base and the side wall when present in the chamber, wherein during operation the generating system is configured to draw the at least one magnetically susceptible member along the base to the side wall connected at the upper end of the base and to move the at least one magnetically susceptible member through the fluid away from the side wall connected at an upper end of the base.

According to a fifth aspect of the invention, there is provided an extractor for extracting material from a fluid, comprising: a fluid chamber comprising an extraction portion and an elution portion, the elution portion having a smaller volume than the extraction portion and having a top opening into a base of the extraction portion, the chamber adapted to contain at least one magnetically susceptible member, the at least one magnetically susceptible member being adapted to bind to material in fluid in the chamber; and a magnetic field generating system associated with the fluid chamber, which generating system is operable to cause the at least one magnetically susceptible member to move within the chamber when present, wherein during operation the generating system is configured to draw the at least one magnetically susceptible member between the extraction and elution portions and around a closed path within the extraction portion.

According to a sixth aspect of the invention, there is provided a system for extracting material from a fluid, comprising: an extractor according to the fourth aspect or fifth aspect; and a controller adapted to carry out the method of any one of the first, second or third aspect using the extractor.

BRIEF DESCRIPTION OF FIGURES

An example of an extractor and a method of extracting material form a fluid are described in detail below, with reference to the accompanying figures, in which:

FIG. 2A to 2F show a perspective view of the extractor;

DETAILED DESCRIPTION

We now describe one example of a method of extracting material from a fluid and a corresponding extractor. The method of extracting material from a fluid and the corresponding extractor are respectively configured to be a process and device used in the extraction of material from a liquid sample. This includes a multi-stage process that uses the extractor and method. In particular, the method and extractor are used to extract DNA from a liquid sample.

The extractor is one component of a larger apparatus that is intended to be used at the point of care. The other components provide other services as well as integrating with the extractor to allow it to be used to carry out the method.

Figure 1:
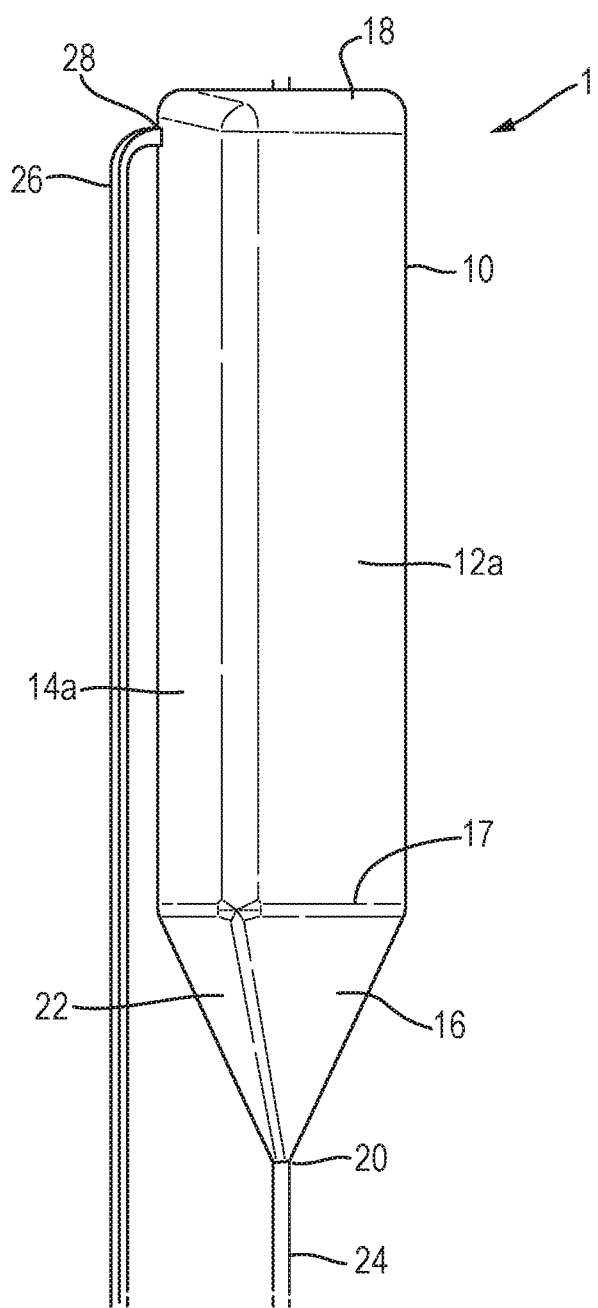
FIG. 1 shows a schematic view of an extractor.

As shown in FIG. 1, the extractor 1 has a fluid chamber 10. The fluid chamber is cuboidal in shape with a first pair of opposing walls 12a, 12b on the front 12a and the back 12b of the chamber, a second pair of opposing walls 14a, 14b on the sides 14a, 14b of the chamber, a base 16 and a top 18. The chamber is orientated so that the base is the lowest part of the chamber causing any contents of the chamber to be pulled towards the base under the influence of gravity. In this manner, matter in a liquid within the chamber will sediment onto the base when the chamber is left undisturbed and there are no other influencing factors.

In the example shown in FIG. 1, the height of the fluid chamber 10 is about 50 millimetres (mm). The width (i.e. the distance between the second pair of opposing walls 14a, 14b of the chamber) is between about 15 mm and about 20 mm in this example, and the depth (i.e. the distance between the front 14a and back 14b of the chamber) is about 8 mm.

The base 16 is not horizontal. Instead, the base is inclined to the vertical. In the example shown in FIG. 1, the base has an incline to the vertical of about 35 degrees (°) and has a vertical component of about 10 mm. The base has an inverted triangular shape with the upper end of the base connected to the front 12a of the chamber 10. This connection is shown as connection 17 in FIG. 1. The lower end of the base at the point of the triangle is connected to a fluid outlet 20 to which the back 12b of the chamber is also connected. This provides a connection of the base to the back of the chamber.

In an alternative arrangement (not shown), a lower section of the back of the chamber is inwardly tapered so that all four sides of the chamber are inwardly tapered giving the lower end of the chamber a conical shape.

The base 16 is connected to the second pair of opposing walls 14a, 14b by a pair of tapered sections 22. The tapered sections are each an inverted triangular shape with their sides connected to the lower end of each wall of the second pair of opposing walls 14a, 14b, the base 16 and the back 12b of the chamber 10. The lower end of each tapered section at the point of the triangle is connected to the fluid outlet 20. Due to the parts of the chamber to which the tapered sections are connected, they have an incline to the vertical.

A fluid outflow channel 24 is connected to the chamber at the fluid outlet 20. A fluid inflow channel 26 is connected to a fluid inlet 28 at an upper end of one of walls of the second pair of opposing walls 14a, 14b. This allows positive pressure to be applied from the top of the chamber to push fluid out of a value (not shown) in the outflow channel, and gravity to be made use of to keep any bubbles generated by the movement and heating of the fluids from leaving the chamber.

The top 18 of the chamber 10 is connected to each of the walls of the first and second pairs of opposing walls 12a, 12b, 14a, 14b. Accordingly, the chamber 10 is sealed apart from the fluid inlet 28 and the fluid outlet 20.

Various components of the apparatus of which the extractor 1 forms a component are manufactured at the same time. This is achieved by using injection moulding. The material used for the injection moulding is polypropylene. As such, the chamber 10 is injection moulded polypropylene. Due to the die used for the moulding process, the back 12b of the chamber is not formed during the injection moulding process. Instead, the back of the chamber is provided by a polypropylene film that is laser welded onto the part produced by injection moulding in which the chamber is formed. A polypropylene film is also used to provide a wall of each of the fluid inflow channel 28 and the fluid outflow channel 24, which are also formed in the part produced by injection moulding.

There are a number of paramagnetic beads 30 inside the chamber 10 with the paramagnetic beads having an overall volume between about 50 micro Litres (μL) and about 200 μL. FIGS. 2A to 2F show only one such bead. The beads are capable of being moved within the chamber by two electromagnets 32, 34. The first electromagnet 32 is located with a pole 33 against the front 12a of the chamber at the connection between the base 16 and the front. The second electromagnet 34 is located with a pole 35 against the back 12b of the chamber.

The poles 33, 35 of the first and second electromagnets 32, 34 are arranged with a vertical offset between their centres. As such, the pole of the second electromagnet is located higher up the chamber 10 than the pole of the first electromagnet meaning that it has a greater vertical distance from the connection of the base 16 and the front 12a of the chamber than the pole of the first electromagnet. In this example, the poles of the electromagnets have a diameter of about 15 mm. and the vertical offset between the centres of the poles is about 12 mm.

Each electromagnet is of course connected to a power supply (not shown) and a control system (not shown) that respectively provides power to each electromagnet and controls each electromagnet. The power supply provides 24 Volts (V) to each electromagnet. The pull that the electromagnets are capable of producing based on this amount of power is a pull of about 3.5 kg.

By the phrase "pull of about 3.5 kg", we intend to mean that each electromagnet is capable of holding an object with a mass of up to about 3.5 kg disposed directly against a pole of the electromagnet directly underneath the electromagnet magnet so that only gravity and the electromagnet act on the object.

The placement of the electromagnets 32, 34 is intended to provide as great a vertical offset between the electromagnets as possible whilst still allowing the extractor to function effectively. Accordingly, if different electromagnets, dimensions or conditions, such as power usage, are used, the vertical offset may be able to be greater than the vertical offset of this example.

Additionally, the placement of the electromagnets 32, 34 causes a strong part of the field produced by each electromagnet to pass through the chamber 10. This is because the field at the poles is stronger than the field beside each electromagnet. In terms of magnetic field lines, the magnetic field lines are densest at the poles with the density decreasing as the distance from the poles decreases.

Figure 2D:
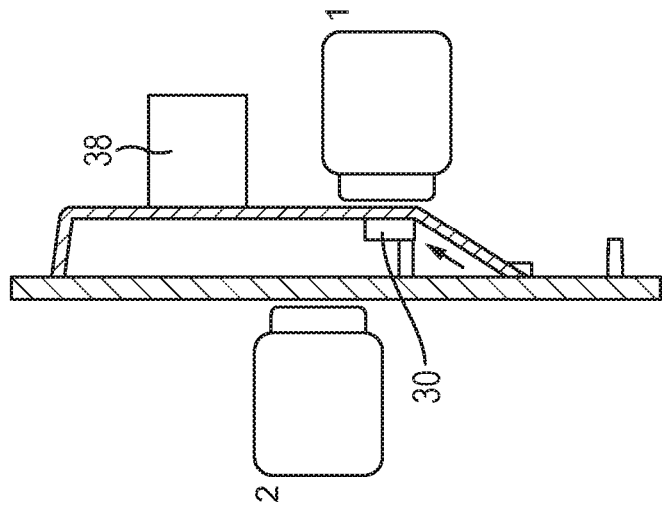
Figure 2E:
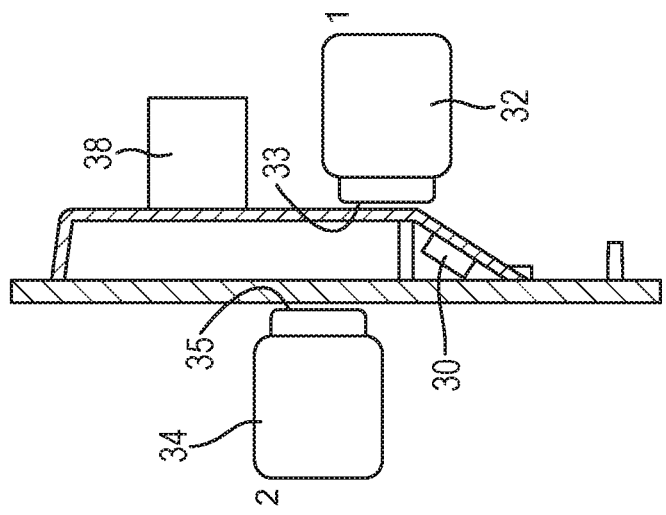
Figure 2F:
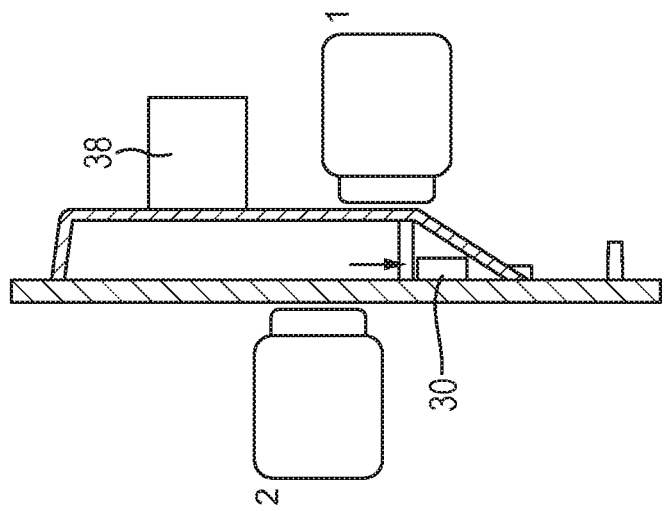

The electromagnets 32, 34 are used to move the paramagnetic beads 30 around the chamber when the chamber 10 is filled with liquid (not shown). As shown in FIGS. 2A and 2E, when the electromagnets are switched off, the paramagnetic beads lie along the base 16 of the chamber. To move paramagnetic beads around the chamber, the first electromagnet 32 is then switched on. This draws the paramagnetic beads up the inclined base 16 along the interior surface of the base to the front 12a of the chamber at the connection 17 between the front and the base (step 101) (see FIGS. 2B and 2F).

The second electromagnet 34 is then turned on and, after a short period of about one to five seconds, the first electromagnet 32 is turned off. This causes the paramagnetic beads 30 to move away from the front 12a of the chamber 10 towards the back 12b of the chamber (step 102) (see FIG. 2C) while avoiding the paramagnetic beads falling away from the front of the chamber before they are pulled towards the back of the chamber.

The paramagnetic beads 30 are then allowed to return to lying along the base by turning off the second electromagnet. This causes the paramagnetic beads to return to the base under the influence of gravity (step 103) (see FIG. 2D). The angle of incline of the base allows the beads to lie along the base without falling down when they fall on to the base.

The electromagnets 32, 34 are each a continuous solenoid type electromagnet and have a core (not shown), such as an iron alloy core, that becomes warm when the electromagnet is switched on. Due to the placement of the pole of each electromagnet against the chamber, each core heats the liquid in the chamber by transfer of heat.

Figure 3:
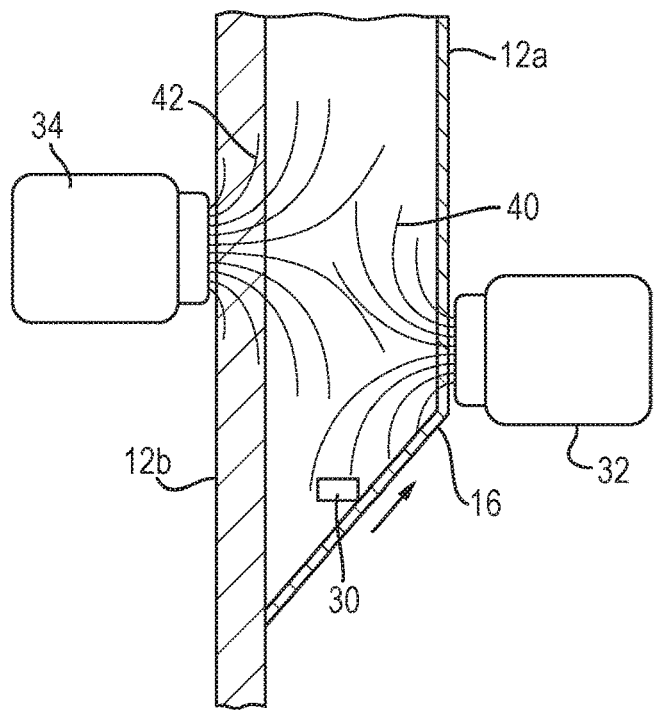
FIG. 3 shows a partial schematic view of the extractor including partial illustrations of magnetic field lines.

Due to the angle of the incline of the base 16 and the placement of the first electromagnet 32, when the paramagnetic beads 30 are drawn up the base by the first electromagnet, they are drawn across the magnetic field at the lower end of the base, and then parallel to the magnetic field as they approach the front 12*a* of the chamber. As shown in FIG. 3, relative to the magnetic field lines 40 of the first electromagnet, which are partially shown in FIG. 3, this movement (indicated by the arrow in FIG. 3) causes the paramagnetic beads to cross the magnetic field lines when being drawn up the lower end of the base and then to follow a path parallel to the magnetic field lines at the upper end of the base.

When the paramagnetic beads are moved by the second electromagnet 34, due to the relative positions of the first electromagnet 32 and second electromagnet, the paramagnetic beads move predominantly parallel to the magnetic field lines 42 of the second electromagnet (also partially shown in FIG. 3). By the phrase "predominantly parallel", it is intended to mean that the movement is more in a direction parallel to the direction of the magnetic field produced by the at least one electromagnet.

Moving the paramagnetic beads towards a pole of the respective electromagnets produces a stronger pull on the beads than if they were just moved through a magnetic field. As such, this allows the sample to have a higher viscosity than a fluid such as water. For example, the fluid is able to be blood or sputum or other body fluids.

The paramagnetic beads 30 are coated with material that has an affinity to DNA and/or RNA, such as streptavidin. This causes DNA or RNA in the liquid in the chamber 10 that comes into contact with the surfaces of the paramagnetic beads to bind to the beads. Instead of moving as a single mass in the magnetic fields of the electromagnets, the paramagnetic beads are dispersed when moving through the sample. This contributes to the mixing of the paramagnetic beads with the liquid in the chamber, maximising the amount of DNA and/or RNA that the beads come into contact with and therefore bind to.

To assist with mixing of liquid in the chamber, there is a vibrator motor 38. The vibrator motor is located above the first electromagnet in physical contact with the front 12*a* of the chamber 10. The motor acts to homogenise the liquid when it is operated, which re-distributes remaining DNA and RNA in the sample making it more likely for it to come into contact with the paramagnetic beads 30.

Figure 4:
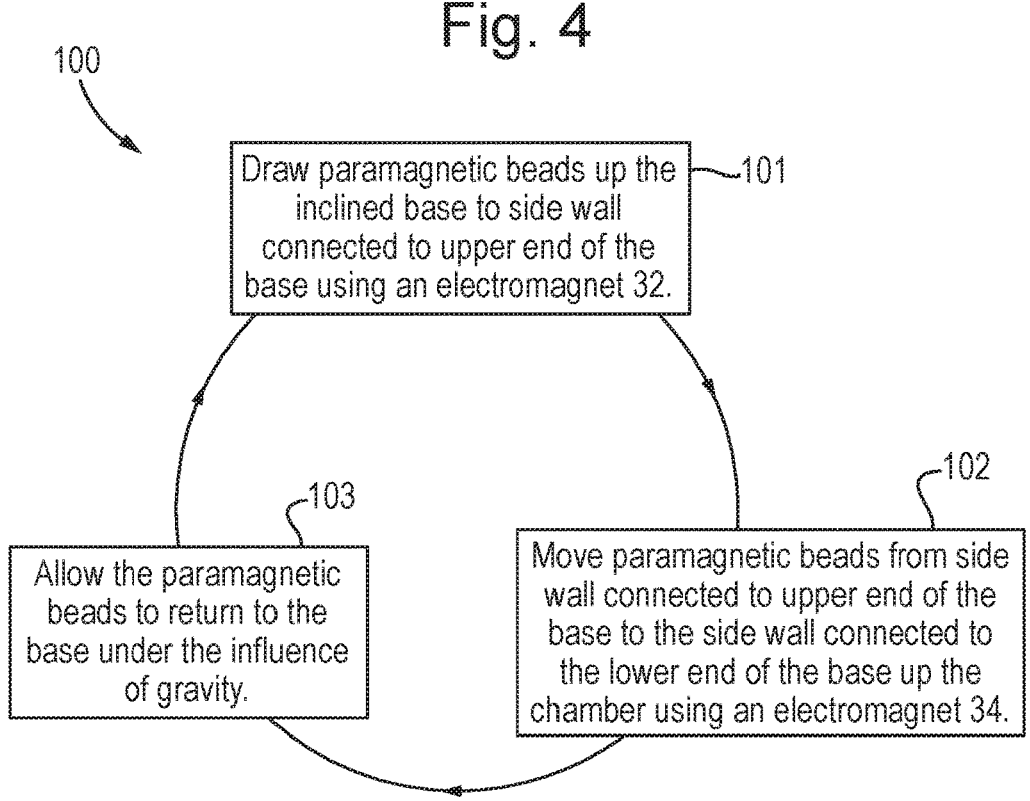
FIG. 4 shows a flow chart of the example method.
Figure 5:
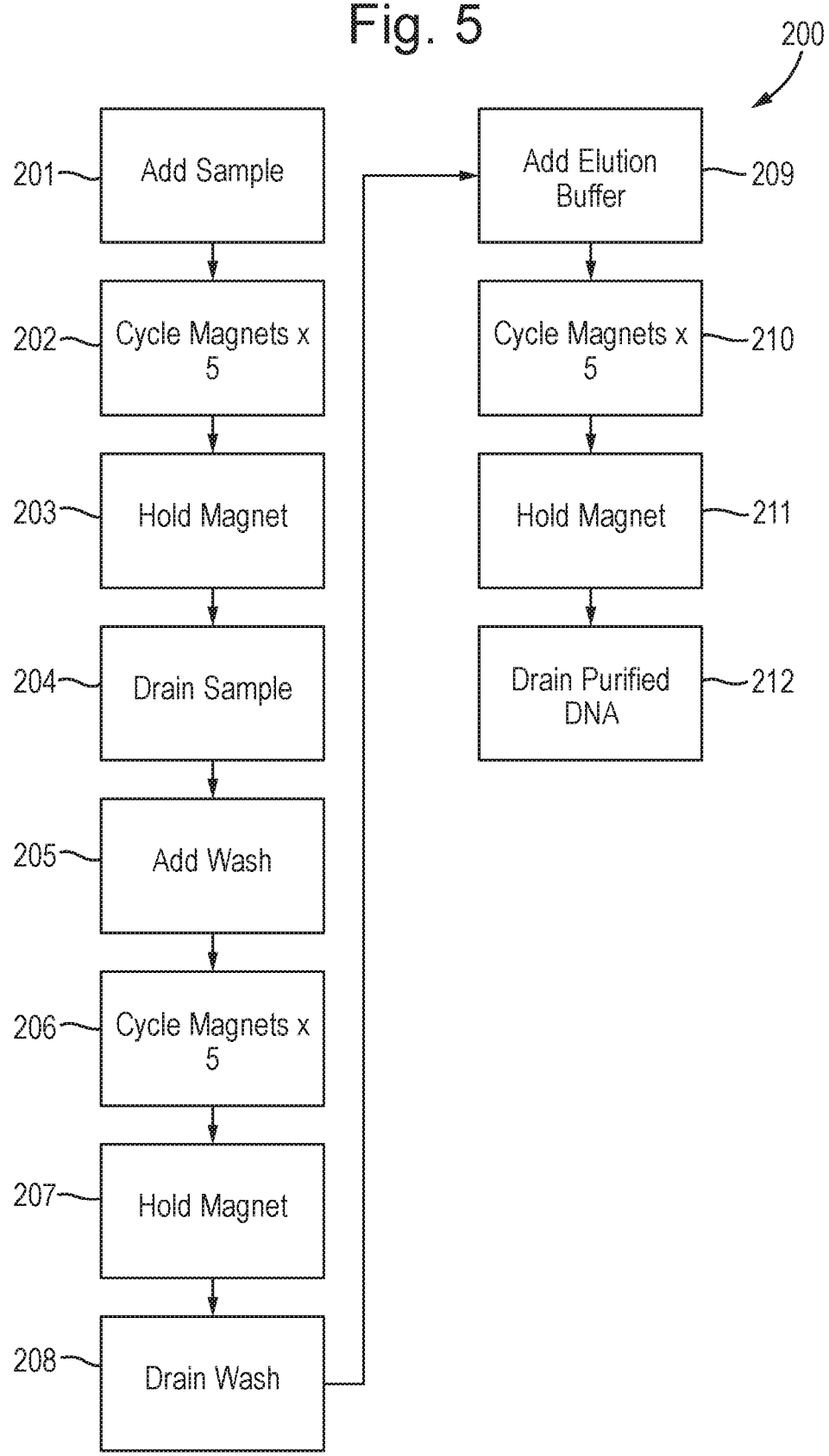
FIG. 5 shows a flow chart of the process of which the method is a part.

As shown in FIG. 4, the paramagnetic beads 30 are moved in a cycle 100 by being drawn up the base 16 to the front 12*a* of the chamber 10, moved to the back 12*b* of the chamber and then allowed to return to the base. This cycle is repeated at various times during a process to separate DNA and/or RNA from a liquid sample. This process 200 is shown in FIG. 5.

The process 200 involves adding 201 the liquid sample to the chamber 10. This is achieved by pumping the sample into the chamber through the inlet 28 from the inflow channel 26.

Once the sample has been added to the chamber 10, the cycle 100 shown in FIG. 4 and described above is run 202. At this point, the cycle is run five times. This moves the paramagnetic beads 30 through the sample causing any DNA and RNA that the beads come in contact with to bind to the beads. The vertical offset of the electromagnets provides a long path relative to the volume of the sample so that as much DNA and RNA binds to the beads as possible.

Additionally, the cycling of the beads round the chamber causes movement and turbulence in the sample. This mixes the sample having a homogenising effect, increasing the likelihood of DNA and RNA in the sample coming in contact with the beads by re-distributing DNA and RNA in the sample.

The paramagnetic beads 30 are then held 203 against the front 12*a* of the chamber 10. This is achieved by drawing the beads to the front of the chamber using the first electromagnet 32. This is to avoid the beads preventing the sample from being drained from the chamber through the outlet 20 and into the outflow channel 24. The beads have a larger than diameter than the outlet so that they cannot fall into the outflow channel 24. However, holding the beads away from the outlet speeds up the draining process.

The sample is then drained 204 from the chamber 10, and a wash fluid is added 205 to the chamber from the inlet 28. The tapered sections 22 assist with the drainage by directing, in this case, the sample towards the fluid outlet 20.

Once the wash fluid has been added to the chamber, the paramagnetic beads 30 are cycled round the chamber as described above. The cycle 100 is again run 206 five times. This is to wash away any waste residue from the surface of the paramagnetic beads.

Following the cycle, the paramagnetic beads 30 are again held 207 against the front 12*a* of the chamber 10 by again using the first electromagnet 32 to draw the beads to the front of the chamber. The wash is then drained 208 from the chamber through the outlet 20. If at any time the beads prevent fluid in the chamber from draining out of the outlet, air is blown into the chamber to dislodge the beads. This is most likely to occur if the beads are not held against the front of the chamber during the draining of a fluid from the chamber.

Once the wash fluid is drained from the chamber 10, a high-salt elution buffer is added 209 to the chamber through the inlet 28. The elution buffer is used to dissociate the DNA and RNA from the surface of the beads. To achieve this, the cycle 100 is run 210 a further five times.

Following the running of the cycle, the paramagnetic beads 30 are again held 211 against the front 12*a* of the chamber 10. The elution buffer now containing the DNA and RNA that was bound to the beads is then drained 212 from the chamber through the outlet 20. Accordingly, this purified DNA and/or RNA is then able to undergo further processing and analysis.

The process 200 shown in FIG. 5 takes about 10 minutes to complete and returns a DNA/RNA yield comparable to known methods.

Additionally, the extractor is able to be used to remove magnetically susceptible material within a sample. This is achieved by attracting such material to the electromagnets.

As an alternative to extracting DNA and/or RNA from a sample, the extractor and process describe above can be used to detect the presence of a material in a fluid. This is able to be achieved by a detection mechanism such as fluorescence.

In a further example, the second electromagnet 34 is moveable. The second electromagnet is moveable along the back 12*b* of the chamber 10. The movement is in a direction along a length of the chamber. This is achieved by the second electromagnet being mounted on a rail (not shown) along which it is able to be moved by a motor (not shown). The range of movement of the second electromagnet includes the ability to move the second electromagnet in line with the base towards the outlet 20, and in some examples to the outlet 20 from a position above the first electromagnet 32. This allows any paramagnetic beads 30 that may be clumped together at the bottom of the chamber during transport to be collected and moved to an alternative position.

Figure 6:
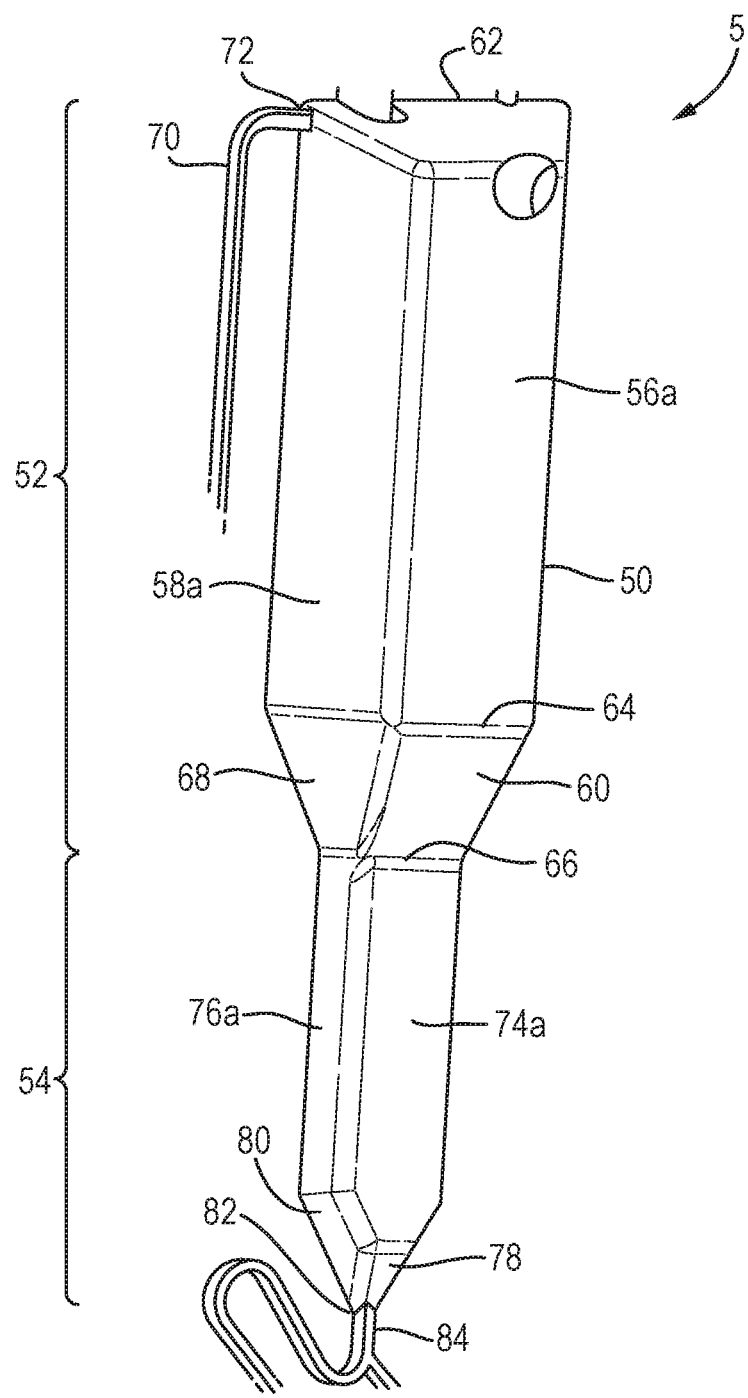
FIG. 6 shows a schematic view of an alternative extractor.

An alternative example extractor 5 is shown in FIG. 6. As with the example extractor shown in FIGS. 1 to 3, this extractor has a fluid chamber 50. However, the fluid chamber of this example has an extraction portion generally illustrated at 52 and an elution portion generally illustrated at 54, which are in fluid communication with each other and form a single continuous chamber.

The extraction portion 52 is similar to the fluid chamber 10 of the example shown in FIGS. 1 to 3. The extraction portion is therefore generally cuboidal in shape with a first pair of opposing walls 56a, 56b on the front 56a and the back 56b of the extraction portion, a second pair of opposing walls 58a, 58b on the sides 58a, 58b of the extraction portion, a base 60 and a top 62. The chamber is orientated so that the base is the lowest part of the extraction portion causing any contents of the extraction chamber to be pulled towards the base under the influence of gravity. In this manner, matter in a liquid within the chamber will sediment towards the base from elsewhere in the extraction portion when the chamber is left undisturbed and there are no other influencing factors.

The base 60 is not horizontal. Instead, the base is inclined to the vertical. In the example shown in FIG. 6, the base has an incline to the vertical of about 35°. The base has an inverted isosceles trapezium shape with the upper (wider) end of the base connected to the front 56a of the extraction portion 52. This connection is shown as connection 64 in FIG. 6. The lower (narrower) end of the base is connected to the elution portion 54 to which the back 56b of the chamber is also connected. The connection between the base and the elution portion is shown as connection 66 in FIG. 6.

The base 60 is connected to the second pair of opposing walls 58a, 58b by a pair of tapered sections 68. The tapered sections are each an inverted acute trapezium shape with their sides connected to the lower end of each wall of the second pair of opposing walls 58a, 58b, the base and the back 56b of the extraction portion 52. The lower end of each tapered section at the narrow end is connected to the elution portion 54. Due to the parts of the chamber 50 to which the tapered sections are connected, they have an incline to the vertical.

A fluid inflow channel 70 is connected to a fluid inlet 72 at an upper end of one of walls of the second pair of opposing walls 58a, 58b of the extraction portion 54. This allows positive pressure to be applied from the top of the chamber to push fluid out of a value (not shown) in an outflow channel, and gravity to be made use of to keep any bubbles generated by the movement and heating of the fluids from leaving the chamber.

Turning to the elution portion 54, this is also generally cuboidal in shape. As such, the elution portion has a first pair of opposing walls 74a, 74b on the front and the back, a second pair of opposing walls 76a, 76b on the sides and a base 78.

As with the base of the extraction portion 52, the base 78 of the elution portion 54 is inclined to the vertical. The base has an inverted triangular shape with the upper end of the base connected to the front 74a of the elution portion 54. The sides of the base are each connected to a tapered section 80. Each tapered section is an acute trapezium shape. The longest side of each tapered section is connected to the back 74b of the elution portion, the upper most side is connected to a side 76a, 76b of the elution portion and the side parallel to the longest side is connected to the front of the elution portion.

At the lowermost point of the base 78, there is a fluid outlet 82. This connects the chamber 50 to a fluid outflow channel 84. Since the only inflows and outflows from the chamber are respectively through the inflow and outflow channels, the chamber 50 is sealed apart from the fluid inlet 70 and fluid outlet.

In the example shown in FIG. 6, the height of the fluid chamber 50 is about 35 mm with the height of the extraction portion 52 being about 20 mm, the height of the elution portion 54 being about 12 mm and the remaining height being associated with sections that tapering or angled sections. The width of the elution portion (i.e. the distance between the second pair of opposing walls 76a, 76b of the elution portion) is about 4.5 mm and the depth (i.e. the distance between the front 74a and back 74b of the chamber) is about 2.0 mm. This gives the elution portion a volume of about 100 μL. The width and depth of the extraction portion is similar to that of the width of the chamber in the example shown in FIGS. 1 to 3. As such, the extraction portion has a volume of about 500 μL.

Figure 7:
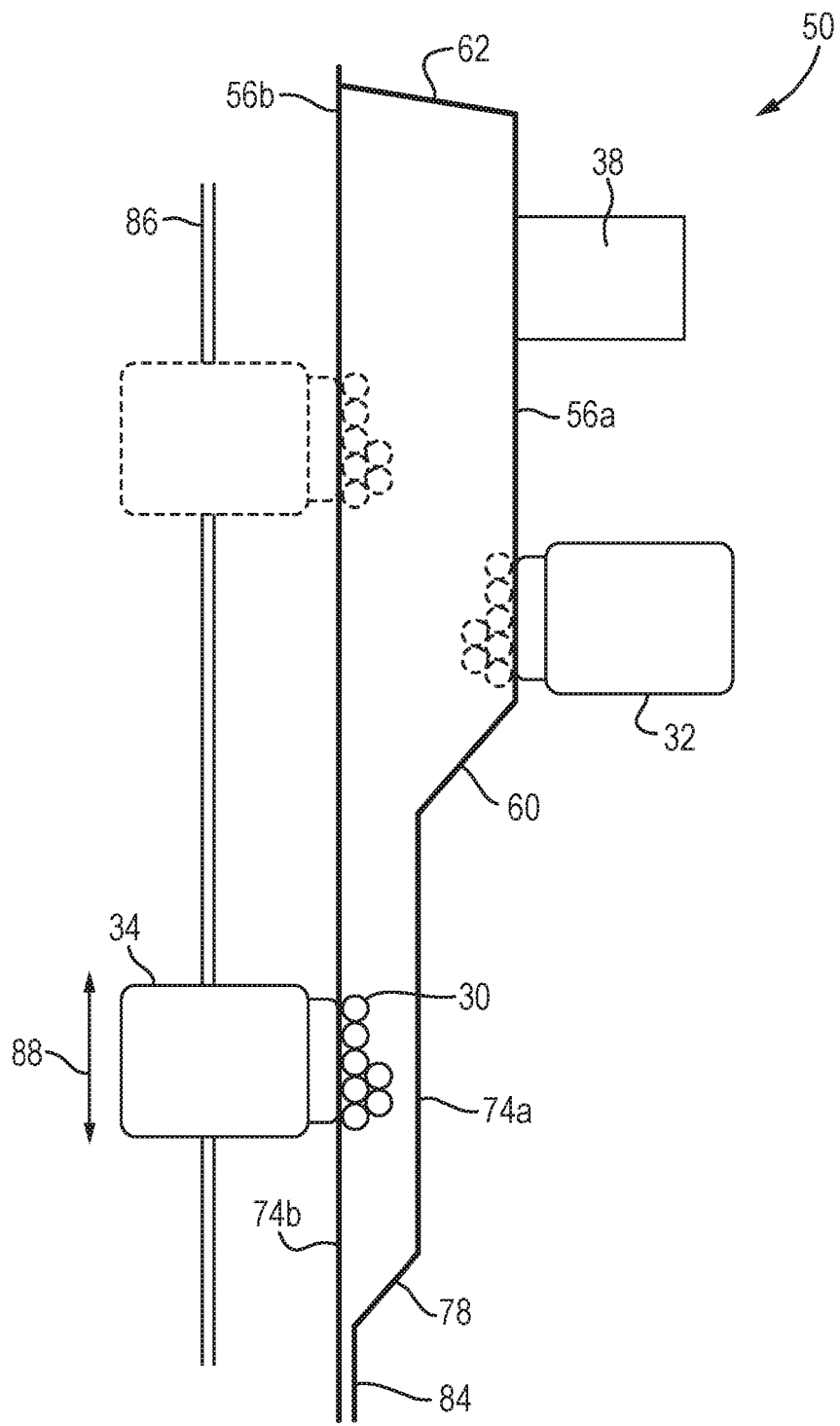
FIG. 7 shows a cross-sectional view of the alternative extractor.

FIG. 7 shows a side-on cross-sectional view of the example extractor shown in FIG. 6. This shows the chamber 50, with a first electromagnet 32 positioned with a poll against the front wall 56a of the extraction portion 52 at the connection between the base 60 and the front wall. A vibration motor 38 is also positioned against this wall between the first electromagnet and the top 62 of the extraction portion.

A second electromagnet 34 is positioned with a pole against the back wall 56b, 74b of the chamber 50. The second electromagnet is moveable along a rail 86 as indicated by arrow 88, the rail having a similar orientation to a longitudinal axis of the chamber. As such, the second electromagnet is moveable between the back wall 74b of the elution portion 54 and the back wall 56b of the extraction portion 52. This is shown in FIG. 7 by the second electromagnet being depicted in a solid line against the back wall of the elution portion and in dashed lines against the back wall of the extraction portion. These positions show example positions at which the second electromagnet is locatable, the position against the back wall of the extraction portion being higher up the extraction portion than the first electromagnet. This means that it has a greater vertical distance from the connection of the base 60 and the front wall 56a of the extraction chamber than the first electromagnet 32 when in this position.

The ability to move the second electromagnet 34 provides an ability to move paramagnetic beads 30 around the inside of the chamber 50 by attraction to the pole of the second electromagnet. This is useful in the process set out in FIG. 8, which sets out a further example process 300 for extracting a material, such as DNA and/or RNA as used in this example, from a liquid sample. This process is now described.

Figure 8:
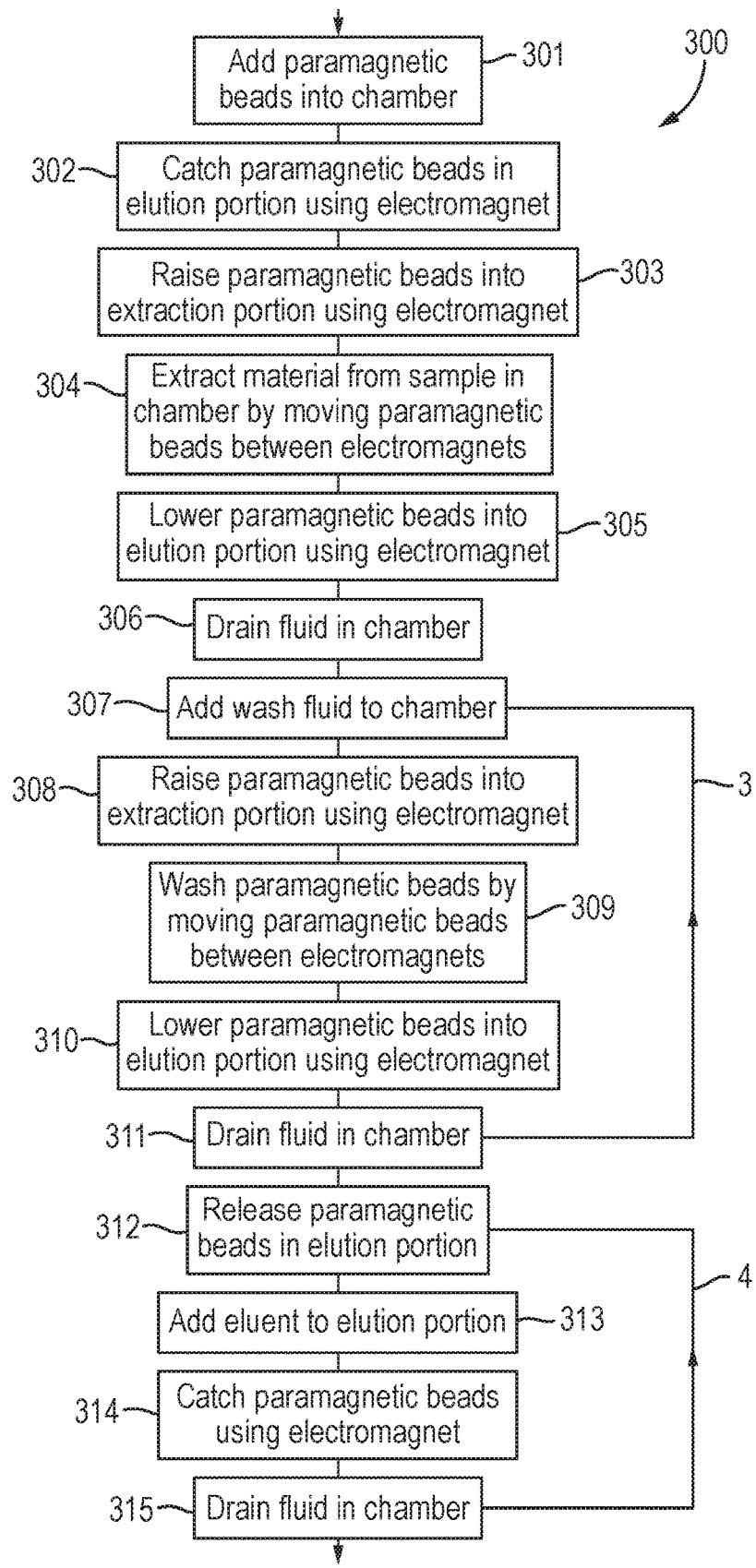
FIG. 8 shows a flow chart of an example process applied using the alternative extractor.

The process 300 shown in FIG. 8 includes the following steps:

The paramagnetic beads 30 are added into the chamber 50, step 301. This is achieved by passing the paramagnetic beads into the chamber through the inflow channel 70 from a different chamber. In this example, the sample is already in the chamber before the paramagnetic beads are introduced into the chamber. In other examples, the sample is added after the paramagnetic beads are introduced into the chamber.

Since the paramagnetic beads 30 are introduced into the chamber 50 near its top, the beads fall under the influence of gravity through the extraction portion 52 and into the elution portion 54. The second electromagnet 34 is located against the back wall 74b of the elution portion and is generating a magnetic field. This causes the paramagnetic beads to be caught, step 302, and held against the back wall of the elution portion by the magnetic field generated by the second electromagnet. When there is fluid in the chamber, the descent of the beads when introduced into the chamber is slowed by the fluid.

The descent is also slowed by the base 60 of the extraction portion. Due to the incline of the base (as mentioned above, about a 35° incline to the vertical) and the resistance and buoyancy provided by the fluid some of the paramagnetic beads may come to rest on the base, or their descent slowed. This improves the likelihood of all of the paramagnetic beads being caught in the magnetic field of the second electromagnet.

Once the paramagnetic beads 30 have been caught, the beads are raised into the extraction portion 52 using the second electromagnet 34, step 303. This is achieved by raising the second electromagnet on the rail 86 into the extraction portion. The second electromagnet is raised to the location described above at a greater vertical distance from the join between the base 60 of the extraction portion and the front wall 56a of the extraction portion than the first electromagnet 32. While the second electromagnet is being moved, the magnetic field generated by the second electromagnet is maintained. This pulls the paramagnetic beads along the back wall 74b of the elution portion and the back wall 56b of the extraction portion due to the attraction to the pole of the second electromagnet induced by the magnetic field generated.

When the second electromagnet 34 has been raised into position in the extraction portion 52, the material in the sample fluid (as set out above, DNA and/or RNA in this example) is extracted from the sample fluid by moving the paramagnetic beads 30 between the electromagnets, step 304. The process used to move the beads between the electromagnets is to first stop the second electromagnet from generating a magnetic field. This means the beads are no longer be held against the back wall 56b of the extraction portion, which causes them to fall under the influence of gravity towards the elution portion 54. After a period of time a magnetic field is generated using the first electromagnet 32. This causes the paramagnetic beads to be drawn towards the pole of the first electromagnet and therefore against the front wall 56a of the extraction portion. This is indicated by the paramagnetic beads depicted in dashed lines against the front wall of the extraction portion in FIG. 7.

Once the paramagnetic beads have had sufficient time to gather against the front wall of the extraction portion, the magnetic field generated by the first electromagnet is removed and the magnetic field generated by the second electromagnet is reinstated. This draws the paramagnetic beads back across the chamber 50 to the location against the back wall of the extraction portion where the second electromagnet is located. This position is indicated in FIG. 7 by the paramagnetic beads shown in dashed lines by the depiction of the second electromagnet in dashed lines. This process is then repeated until the paramagnetic beads have been cycled around a predetermined number of times. Unlike when the second electromagnet stops generating the magnetic field, there is not intended to be any time between the magnetic field generated by the first electromagnet being removed and the magnetic field generated by the second electromagnet being reinstated.

The path followed by the paramagnetic beads 30 during the extraction of the material from the sample fluid is generally triangular in shape. The paramagnetic beads fall in a generally vertical direction. Given that the rate of descent of the beads in the fluid is approximately known due to the properties of the fluid generally being known, the timing of when the first electromagnet generates its magnetic field is controlled so that the magnetic field is generated when the beads are approximately in line with the first electromagnets. The beads then move back across the chamber 50 in an approximately straight line to their initial position. This forms a path along with the beads travel that is approximately the shape of a right-angle triangle. In some examples the beads are allowed to fall further before the magnetic field is generated by the first electromagnet to draw the beads to the front wall of the extraction portion.

Once the predetermined number of cycles has been completed, the paramagnetic beads 30 are lowered back into the elution portion 54 of the chamber 50, step 305. This is achieved by the reverse process by which the beads are raised into the extraction portion 52. As such, the beads are held against the back wall 56b of the extraction portion by the magnetic field generated by the second electromagnet 34. The second electromagnet is lowered on the rail 86 back into position against the back wall 74b of the elution portion causing the beads to also be pulled into the elution portion due to the pull induced by the magnetic field.

Following the lowering of the paramagnetic beads 30 into the elution portion 54, the fluid in the chamber 50 is drained, step 306, by removing the fluid through the fluid outflow channel 84 by the exertion of positive pressure through the fluid inflow channel 70. A wash fluid is then added to the chamber, step 307.

Once the wash fluid is added to the chamber, the paramagnetic are again raised into the extraction portion, step 308, using the process described above. The paramagnetic beads are then washed by moving the beads between the electromagnets, step 309. This is achieved using the same process used to move the beads by which the material is extracted from the fluid sample as described above. The cycle of moving the beads between the electromagnets is again completed a predetermined number of times. When the predetermined number of cycles is completed, the beads are lowered again into the elution portion of the chamber, step 310, as described above. The wash fluid is then drained from the chamber, step 311, by the process described above.

The process of adding wash fluid, raising the paramagnetic beads 30, washing the paramagnetic beads, lowering the paramagnetic beads and draining the wash fluid of steps 307 to 311 is then repeated as many times as needed. This is indicated in FIG. 8 by the arrow 3.

When the washing cycle is completed, the paramagnetic beads 30 are released in the elution portion 54 of the chamber 50, step 312. To achieve this, the magnetic field generated by the second electromagnet 34 is removed. This causes the beads to drop to the base 78 of the elution portion under the influence of gravity since they are no longer supported by a magnetic field. An eluent is then added into the chamber, step 313. Only enough eluent is added to the chamber to fill the elution portion. In this example, this means that a volume of about 100 μL or less of eluent is added into the chamber.

The eluent is added to the chamber 50 either through the fluid inflow channel 70 or through the fluid outflow channel 84. The adding of the eluent to the chamber causes the paramagnetic beads 30 to move due to the turbulence in the eluent fluid and general disturbance caused by the eluent being added. Contact between the eluent and the paramagnetic beads causes the material (DNA and/or RNA) adhered to the paramagnetic beads to become dissociated from the beads and therefore to enter the eluent fluid.

Once the eluent has been added to the elution portion 54 of the chamber 50, the paramagnetic beads 30 are caught using the second electromagnet 34, step 314. This is achieved by generating a magnetic field with the second electromagnet causing the paramagnetic beads to be pulled against the back wall 76b of the elution portion in the location where the second electromagnet 34 is positioned. When the paramagnetic beads have been caught, the fluid is again drained from the chamber, step 315, using the process described above.

The process of releasing the paramagnetic beads 30, adding eluent, catching the paramagnetic beads and draining fluid of steps 312 to 315 is repeated as many times as is needed. This is indicated in FIG. 8 by arrow 4. When as many repeats as necessary have been completed, the process is complete and further processing is conducted on the eluent, now an eluate containing the material, in another part of the system. At this stage the paramagnetic beads may be removed from the chamber 50.

The invention claimed is:

1. A method of extracting material from a fluid, the fluid being held within a fluid chamber, the method comprising:
    drawing, with a magnetic field generating system, at least one magnetically susceptible member through the fluid around a closed path between at least three points in the chamber, said at least one member being adapted to bind to material in fluid in the chamber, wherein
    the at least three points are arranged relative to each other in a shape having at least two dimensions, the magnetic field generating system being configured to move the at least one magnetically susceptible member directly between the at least three points, material in the fluid binding to the at least one magnetically susceptible member when it comes into contact with the at least one member as it moves through the fluid, and wherein the magnetic field generating system comprises at least one electromagnet, and the magnetic field generating system is configured to draw the at least one magnetically susceptible member to two of the at least three points using a magnetic field and to allow the at least one magnetically susceptible member to travel to the third point of the at least three points without using a magnetic field, the method further comprising heating the fluid in the chamber with heat produced by the at least one electromagnet.

2. The method according to claim 1, wherein the at least one magnetically susceptible member is allowed to travel to the third point of the at least three points under the influence of gravity.

3. The method according to claim 1, wherein movement of the at least one magnetically susceptible member caused by operation of the magnetic field generating system is predominantly parallel to the direction of the magnetic field produced by the at least one electromagnet.

4. The method according to claim 1, wherein the fluid chamber comprises a side wall connected to a base and orientated such that contents of the chamber are pulled towards the base under the influence of gravity, the base being inclined to the vertical, and wherein the step of drawing the at least one magnetically susceptible member through the fluid around the closed path between the at least three points in the chamber comprising:
    drawing, with the magnetic field generating system, the at least one magnetically susceptible member along the base to the side wall connected at an upper end of the base;
    moving, with the magnetic field generating system, the at least one magnetically susceptible member through the fluid away from the side wall connected at the upper end of the base; and
    allowing the at least one magnetically susceptible member to return to the base.

5. The method according to claim 4, wherein moving the at least one magnetically susceptible member through the fluid away from the side wall connected at the upper end of the base comprises moving the at least one magnetically susceptible member across the chamber to the side wall above the connection to the base at the lower end of the base; and/or wherein the magnetically susceptible member is moved vertically away from the base when moved away from the side wall connected at the upper end of the base; and/or wherein the steps of drawing the magnetically susceptible member along the base, moving said member through the fluid away from the side wall and allowing said member to return to the base are repeated in a cycle; and/or wherein the at least one magnetically susceptible member is allowed to return to the base under the influence of gravity; and/or wherein the side wall comprises a pair of opposing side walls, one side wall of which is connected to the upper end of the base and the other side wall of which is connected to the lower end of the base.

6. The method according to claim 4, wherein the at least one magnetically susceptible member is drawn along the base by a first electromagnet and moved through the fluid away from the side wall by a second electromagnet.

7. The method according to claim 1, wherein the fluid chamber comprises an extraction portion and an elution portion, the elution portion having a smaller volume than the extraction portion and having a top opening into a base of the extraction portion, the method further comprising:
    drawing, with the magnetic field generating system, the at least one magnetically susceptible member between the extraction and elution portions of the chamber; and
    removing material bound to the at least one magnetically susceptible member from the at least one magnetically susceptible member when in the elution portion by replacing the fluid in the chamber with an eluent held in only the elution portion.

8. The method according to claim 7, wherein the at least three points form a configuration corresponding to the vertices of a triangle.

9. The method according to claim 8, wherein two of the vertices have the same separation along a longitudinal axis of the chamber from the base of the extraction portion of the chamber.

10. The method according to claim 9, wherein the third vertex has a greater separation along the longitudinal axis of the chamber from the base of the extraction portion of the chamber than the other two vertices, and/or wherein the at least one magnetically susceptible member is allowed to move between the third vertex and one of the two other vertices under the influence of gravity.

11. The method according to claim 7, wherein the step of drawing the at least one magnetically susceptible member through the fluid around the closed path between the at least three points in the chamber comprises:

moving, with the magnetic field generating system, the at least one magnetically susceptible member through the fluid from a first side wall of the extraction portion of the chamber away from the first side wall.

12. The method according to claim 11, wherein the first side wall is a single continuous wall forming a side wall of the extraction portion and the elution portion, and/or wherein moving the at least one magnetically susceptible member through the fluid away from the side comprises moving the at least one magnetically susceptible member across the chamber to a second side wall, the second side wall being an opposing side wall of the extraction portion to the first side wall.

13. The method according to claim 7, wherein drawing the at least one magnetically susceptible member between the extraction and elution potions of the chamber comprises moving at least one electromagnet of the at least one electromagnets between the extraction and elution portion while retaining the at least one magnetically susceptible member in a magnetic field generated by said at least one electromagnet.

14. The method according to claim 7, wherein the base of the extraction portion is shaped to form a funnel, a narrow end of the funnel being connected to the elution portion and a wide end of the funnel being connected to side walls of the extraction portion.

15. The method according to claim 1, wherein the at least one magnetically susceptible member is at least one paramagnetic member and/or further comprising mixing the fluid with a mixing system, and/or wherein the material is DNA and/or RNA.

16. The method according to claim 1, wherein the at least one magnetically susceptible member has a coating to which material in fluid in the chamber binds.

17. The method according to claim 1, wherein the fluid is a liquid such as fungal liquor, water, milk, wine, honey, syrup or body fluids, including serum, urine, vaginal fluid, semen, pus, cerebral fluid, blood or sputum.

18. A method of extracting material from a fluid, the fluid being held within a fluid chamber comprising a side wall connected to a base and orientated such that contents of the chamber are pulled towards the base under the influence of gravity, the base being inclined to the vertical, the method comprising the steps:
drawing, with a magnetic field generating system, at least one magnetically susceptible member adapted to bind to material in fluid in the chamber along the base to the side wall connected at an upper end of the base;
moving, with said magnetic field generating system, the at least one magnetically susceptible member through the fluid away from the side wall connected at the upper end of the base to a further position to move the at least one magnetically susceptible member directly between at least three points, wherein the magnetic field generating system is configured to draw the at least one magnetically susceptible member to two of the at least three points using a magnetic field and to allow the at least one magnetically susceptible member to travel to the third point of the at least three points without using a magnetic;
allowing the at least one magnetically susceptible member to return to the base; and
heating, with at least one electromagnet comprised by the magnetic field generating system, fluid in the chamber.

19. A method of extracting material from a fluid, the fluid being held within a fluid chamber comprising an extraction portion and an elution portion, the elution portion having a smaller volume than the extraction portion and having a top opening into a base of the extraction portion, the method comprising the steps:
drawing, with a magnetic field generating system, at least one magnetically susceptible member adapted to bind to material in fluid in the chamber directly between at least three points to draw the at least one magnetically susceptible member between the extraction and elution portions of the chamber and around a closed path within the extraction portion the magnetic field generating system is configured to draw the at least one magnetically susceptible member to two of the at least three points using a magnetic field and to allow the at least one magnetically susceptible member to travel to the third point of the at least three points without using a magnetic;
moving, with said magnetic field generating system, the at least one magnetically susceptible member through the fluid between side walls of the chamber;
heating, with at least one electromagnet comprised by the magnetic field generating system, fluid in the chamber; and
removing material bound to the at least one magnetically susceptible member from the at least one magnetically susceptible member when in the elution portion by replacing the fluid in the chamber with an eluent held in only the elution portion.

20. An extractor for extracting material from a fluid, comprising:
a fluid chamber comprising a side wall connected to a base and orientated such that contents of the chamber are pulled towards the base under the influence of gravity, the base being inclined to the vertical, the chamber being adapted to contain at least one magnetically susceptible member, said at least one magnetically susceptible member being adapted to bind to material in fluid in the chamber; and
a magnetic field generating system associated with the fluid chamber, which generating system is operable to cause the at least one magnetically susceptible member to move around a closed path including the base and the side wall when present in the chamber and a further position to move the at least one magnetically susceptible member directly between at least three points, wherein during operation the generating system is configured to draw the at least one magnetically susceptible member along the base to the side wall connected at the upper end of the base and to move the at least one magnetically susceptible member through the fluid away from the side wall connected at an upper end of the base and the magnetic field generating system is configured to draw the at least one magnetically susceptible member to two of the at least three points using a magnetic field and to allow the at least one magnetically susceptible member to travel to the third point of the at least three points without using a magnetic field, wherein the magnetic field generating system comprises at least one electromagnet arranged in use to generate heat such that fluid in the chamber is heated in use by heat produced by the at least one electromagnet.

21. An extractor for extracting material from a fluid, comprising:
a fluid chamber comprising an extraction portion and an elution portion, the elution portion having a smaller volume than the extraction portion and having a top opening into a base of the extraction portion, the chamber adapted to contain at least one magnetically susceptible member, the at least one magnetically susceptible member being adapted to bind to material in fluid in the chamber; and a magnetic field generating system associated with the fluid chamber, which generating system is operable to cause the at least one magnetically susceptible member to move within the chamber when present, wherein during operation the generating system is configured to move the at least one magnetically susceptible member directly between at least three points to draw the at least one magnetically susceptible member between the extraction and elution portions and around a closed path within the extraction portion, wherein the magnetic field generating system is configured to draw the at least one magnetically susceptible member to two of the at least three points using a magnetic field and to allow the at least one magnetically susceptible member to travel to the third point of the at least three points without using a magnetic field, and the magnetic field generating system comprises at least one electromagnet arranged in use to generate heat such that fluid in the chamber is heated in use by heat produced by the at least one electromagnet.

22. A system for extracting material from a fluid, comprising:

an extractor according to claim 20; and wherein the system is adapted to carry out the method of drawing, with a magnetic field generating system, at least one magnetically susceptible member through the fluid around a closed path between at least three points in the chamber, said at least one member being adapted to bind to material in fluid in the chamber, wherein the at least three points are arranged relative to each other in a shape having at least two dimensions, the magnetic field generating system being configured to move the at least one magnetically susceptible member directly between the at least three points, material in the fluid binding to the at least one magnetically susceptible member when it comes into contact with the at least one member as it moves through the fluid using the extractor, and wherein the magnetic field generating system comprises at least one electromagnet, and the magnetic field generating system is configured to draw the at least one magnetically susceptible member to two of the at least three points using a magnetic field and to allow the at least one magnetically susceptible member to travel to the third point of the at least three points without using a magnetic field, the method further comprising heating the fluid in the chamber with heat produced by the at least one electromagnet.

23. A system for extracting material from a fluid, comprising:

an extractor according to claim 21; and wherein the system is adapted to carry out the method of drawing, with a magnetic field generating system, at least one magnetically susceptible member through the fluid around a closed path between at least three points in the chamber, said at least one member being adapted to bind to material in fluid in the chamber, wherein the at least three points are arranged relative to each other in a shape having at least two dimensions, the magnetic field generating system being configured to move the at least one magnetically susceptible member directly between the at least three points, material in the fluid binding to the at least one magnetically susceptible member when it comes into contact with the at least one member as it moves through the fluid using the extractor, and wherein the magnetic field generating system comprises at least one electromagnet, and the magnetic field generating system is configured to draw the at least one magnetically susceptible member to two of the at least three points using a magnetic field and to allow the at least one magnetically susceptible member to travel to the third point of the at least three points without using a magnetic field, the method further comprising heating the fluid in the chamber with heat produced by the at least one electromagnet.

* * * * *